United States Patent
Greff

(10) Patent No.: US 8,295,942 B2
(45) Date of Patent: Oct. 23, 2012

(54) METHOD AND APPARATUS FOR REDUCING EXCESS ADIPOSE TISSUE

(75) Inventor: Daniel Greff, Mere (FR)

(73) Assignee: Biopass S.A., Luxembourg (LU)

( * ) Notice: Subject to any disclaimer, the term of this patent is extended or adjusted under 35 U.S.C. 154(b) by 568 days.

(21) Appl. No.: 12/444,518

(22) PCT Filed: Oct. 8, 2007

(86) PCT No.: PCT/FR2007/001639
§ 371 (c)(1),
(2), (4) Date: Apr. 6, 2009

(87) PCT Pub. No.: WO2008/043907
PCT Pub. Date: Apr. 17, 2008

(65) Prior Publication Data
US 2011/0066087 A1      Mar. 17, 2011

(30) Foreign Application Priority Data
Oct. 6, 2006  (FR) ...................... 06 08815

(51) Int. Cl.
*A61F 7/00* (2006.01)
*A61F 7/02* (2006.01)
(52) U.S. Cl. .......................... 607/100; 601/15
(58) Field of Classification Search .................... 601/15; 607/100
See application file for complete search history.

(56) References Cited

U.S. PATENT DOCUMENTS

| | | | | |
|---|---|---|---|---|
| 5,084,003 A | * | 1/1992 | Susic | 600/13 |
| 5,411,541 A | * | 5/1995 | Bell et al. | 607/104 |
| 5,660,836 A | * | 8/1997 | Knowlton | 424/400 |
| 5,778,894 A | * | 7/1998 | Dorogi et al. | 128/898 |
| 6,387,380 B1 | * | 5/2002 | Knowlton | 424/400 |
| 7,740,574 B2 | * | 6/2010 | Pilla et al. | 600/13 |
| 2009/0312676 A1 | * | 12/2009 | Rousso et al. | 601/15 |

FOREIGN PATENT DOCUMENTS

| | | |
|---|---|---|
| FR | 2 616 064 | 6/1987 |
| FR | 2 684 547 | 12/1991 |
| FR | 2 855 415 | 5/2003 |
| WO | WO 02/087692 | 11/2002 |
| WO | WO 2004/108210 | 12/2004 |
| WO | WO 2006/103707 | 10/2006 |

OTHER PUBLICATIONS

International Search Report dated May 9, 2008, in PCT application.

* cited by examiner

*Primary Examiner* — Roy Gibson
*Assistant Examiner* — Kaitlyn Smith
(74) *Attorney, Agent, or Firm* — Young & Thompson

(57) ABSTRACT

The adipose areas of the body are simultaneously subjected to lipolysis, through the action of an apparatus that generates low-frequency electromagnetic waves, to extraction, out of the adipose cells, of the fatty acids released by the lipolysis, and to drainage of the fatty acids to the vascular and lymphatic system, through the action of a pressotherapy apparatus.

2 Claims, 1 Drawing Sheet

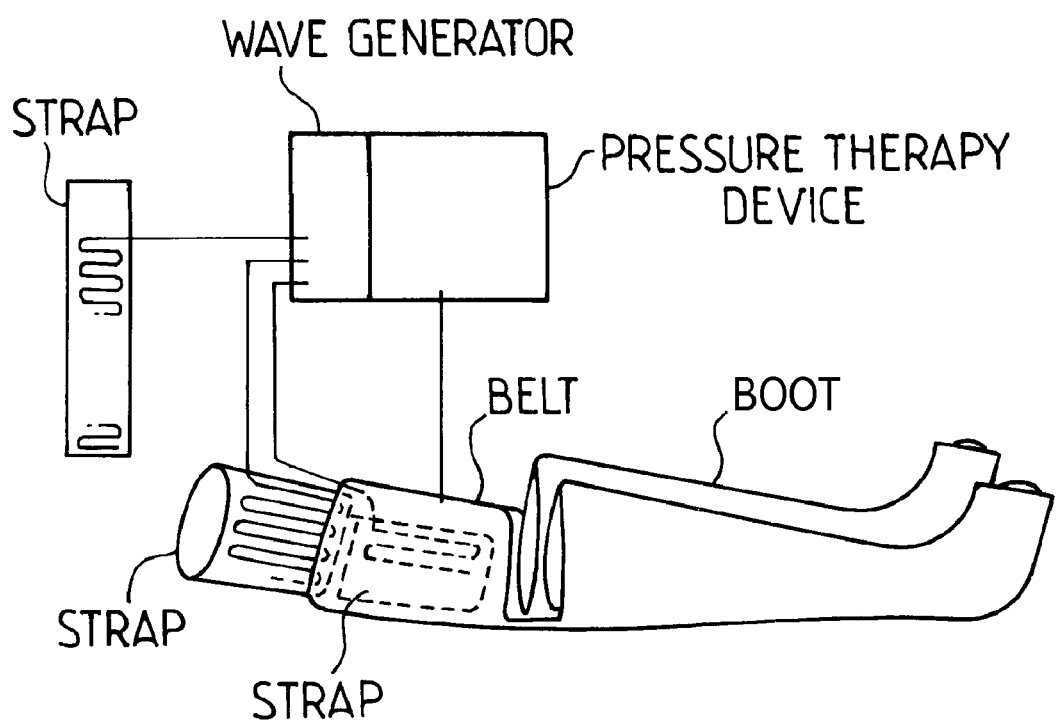

METHOD AND APPARATUS FOR REDUCING EXCESS ADIPOSE TISSUE

BACKGROUND AND BRIEF SUMMARY OF THE INVENTION

The invention relates to a process and a device for the reduction of adipose overloads.

The document FR 2 855 415 describes an electrical device for the reduction of adipose overloads comprising insulating straps in which a conductor is arranged in successive strands that are essentially parallel to one another, whereby a low-voltage, low-frequency alternating current passes through the conductor. The electromagnetic field that is created by the alternating current has a lipolytic and calorigenic action.

However, despite certain results on the reduction of the fat-body mass, the effectiveness of this device remains limited.

One of the purposes of the invention is to propose a device for the reduction of adipose overloads that combines a purely physical, non-traumatizing, non-invasive, but effective complementary action with the action of the electromagnetic field.

The invention has as its object a process for the reduction of adipose overloads, characterized in that the adipose zones of the body are simultaneously subjected to lipolysis, by the action of a low-frequency electromagnetic wave-generating device, and to an extraction, outside of the adipose cells, of fatty acids that are released by lipolysis, and to their draining off toward the vascular and lymphatic system, by the action of a pressure-therapy device.

Advantageously, the electromagnetic waves have a frequency that is less than 100 Hz, and the pressure-therapy device has a double pressure gradient.

The invention also has as its object a device for the implementation of the above-cited process, characterized in that it comprises:

A low-frequency electromagnetic wave generator;
Insulating straps for the envelopment of the adipose zones of the body, equipped with a conductor that is folded into successive strands that are arranged alternately in one direction and then in the other, and
A pressure-therapy device that comprises two boots and an abdominal belt and that is superimposed on said straps.

The invention is described below in a non-limiting embodiment.

BRIEF DESCRIPTION OF THE DRAWINGS

FIG. 1 shows various structures noted throughout the specification.

DETAILED DESCRIPTION OF THE INVENTION

The device for the reduction of the adipose overloads essentially consists of the combination of an electrical subassembly and a mechanical subassembly.

The electrical subassembly, analogous to the one of document FR 2 855 415 to which reference is made, comprises an electromagnetic wave generator of low frequency, less than 100 Hz, for example 50 Hz, and insulating straps that are designed to envelope the adipose zones of the body at the arms, the abdomen, thighs, and calves. These straps are each equipped with a conductor that is folded into successive strands that are arranged alternately in one direction and then in the other. The conductor is incorporated into a thermostable insulating tissue, covered by a fireproof plastic protection.

The conductors are supplied by the generator, under low voltage, 40 V for example, and under low frequency, 50 Hz for example.

The passage of the current into the conductors creates an electrostatic field on the surface of the straps and an electromagnetic field that stimulate the biological mechanisms of lipolysis, thus ensuring a selective reduction of the fat-body mass.

The mechanical subassembly is a pressure-therapy device with a double pressure gradient. It consists of two boots and an abdominal belt. Each of the boots comprises, for example, 10 inflatable compartments, and the belt, comprising, for example, 3 inflatable compartments, is connected to the boots. The pressure-therapy subassembly is superimposed on the straps of the electrical subassembly.

The double pressure gradient corresponds, on the one hand, to the gradual reduction of pressure between the first inflatable compartment, at the level of the base, and the last inflatable compartment, at the top of the boots, and, on the other hand, to the gradual increase of the pressure in each inflatable compartment as the inflation cycles proceed.

This pressure gradient technique avoids the tourniquet effect that is produced by the pressure-therapy devices without a pressure gradient.

The operation of the device for the reduction of adipose overloads is analyzed in the following manner:

The electrical subassembly stimulates lipolysis, i.e., the destocking of fats by release of fatty acids within adipose cells;
The mechanical subassembly, by the effect of mechanical pressure, improves the evacuation of fatty acids outside of the adipose cells and drains off the fatty acids that are released into the adipose tissue toward the vascular and lymphatic system.

Lipolysis is a complex biological process. It is dependent upon two kinds of adipocytary membrane sensors:

The alpha-adrenergic receptors that control the stocking of fats in the adipocytes;
The beta-adrenergic receptors that control the destocking of the fats that are contained in the adipocytes.

The low-frequency electromagnetic waves (50 Hz) are able to stimulate specifically the beta-adrenergic receptors and thus to promote, biologically, the adipocytary lipolysis. These waves act in a non-invasive, inoffensive, and painless manner to ensure a tapering function.

The draining-off function of the mechanical subassembly, whereby the two subassemblies function simultaneously, is combined with this slimming function of the electrical subassembly.

The pressure-therapy technique with a double pressure gradient actually allows a good extraction, outside of the adipose cell, of fatty acids that are released by lipolysis, and a good evacuation of these fatty acids toward the vascular and lymphatic system. This technique, which performs a massage by compression and decompression, activates the blood and lymphatic circulation and promotes the draining off of fatty acids that have been released by lipolysis.

By way of indication, tests carried out on a group of 36 subjects at a rate of two weekly one-hour sessions for six weeks, without massage and a dietary regimen, have made it possible to note a mean loss by weight of 6.2% and a mean loss of fat-body mass of 12.4%, which reflects a very clear reduction of the adipose overloads.

These tests show a quasi-specific reduction of the fat-body mass without significant modification of the lean-body mass. It therefore involves a slimming process that concerns only the adipose overloads and not a weight loss process.

The invention claimed is:

1. A device for the reduction of adipose overloads, comprising:

A low-frequency electromagnetic wave generator;

Insulating straps for the envelopment of the adipose zones of the body, equipped with a conductor that is folded into successive strands that are arranged alternately in one direction and then in the other, and A pressure-therapy device that comprises two boots and an abdominal belt, wherein the abdominal belt comprises at least one of said straps, wherein the electromagnetic waves generated by the electromagnetic wave generator have a frequency that is less than 100 Hz, and wherein the pressure-therapy device has a double pressure gradient.

2. A method of using a device for the reduction of adipose overloads, the device comprising, A low-frequency electromagnetic wave generator, Insulating straps for the envelopment of the adipose zones of the body, equipped with a conductor that is folded into successive strands that are arranged alternately in one direction and then in the other, A pressure-therapy device that comprises two boots and an abdominal belt, wherein the abdominal belt comprises at least one of said straps, wherein the electromagnetic waves generated by the electromagnetic wave generator have a frequency that is less than 100 Hz, and wherein the pressure-therapy device has a double pressure gradient, the method comprising:

placing the boots and abdominal belt onto a person and over adipose zones containing fatty acids, generating an electromagnetic field using the electromagnetic wave generator and the conductor folded into successive strands by passing an electric current into the conductor, subjecting the adipose zones to the electromagnetic field, and simultaneously massaging the adipose zones using the double pressure gradient of the pressure-therapy device by variously increasing and decreasing the pressure gradient.

* * * * *